(12) United States Patent
Carrell et al.

(10) Patent No.: US 9,034,161 B2
(45) Date of Patent: May 19, 2015

(54) SPERM SEPARATION DEVICES AND ASSOCIATED METHODS

(71) Applicants: Douglas T. Carrell, Salt Lake City, UT (US); Luke Simon, Salt Lake City, UT (US)

(72) Inventors: Douglas T. Carrell, Salt Lake City, UT (US); Luke Simon, Salt Lake City, UT (US)

( * ) Notice: Subject to any disclaimer, the term of this patent is extended or adjusted under 35 U.S.C. 154(b) by 0 days.

(21) Appl. No.: 13/975,033

(22) Filed: Aug. 23, 2013

(65) Prior Publication Data

US 2014/0166486 A1    Jun. 19, 2014

Related U.S. Application Data

(60) Provisional application No. 61/692,647, filed on Aug. 23, 2012.

(51) Int. Cl.
*G01N 27/447*     (2006.01)
*C12M 1/00*       (2006.01)
*C12N 5/071*      (2010.01)

(52) U.S. Cl.
CPC .............. *G01N 27/447* (2013.01); *C12M 47/04* (2013.01); *C12N 5/0612* (2013.01)

(58) Field of Classification Search
CPC ........... G01N 27/447–27/453; A61B 10/0058; C12Q 5/061
USPC .................................. 204/450–553, 600–650
See application file for complete search history.

(56) References Cited

U.S. PATENT DOCUMENTS

| | | | |
|---|---|---|---|
| 7,276,329 B2 | 10/2007 | Cumming | |
| 7,838,210 B2 | 11/2010 | Ludwig et al. | |
| 2003/0175917 A1 | 9/2003 | Cumming | |
| 2003/0203408 A1 | 10/2003 | Williams et al. | |
| 2007/0026379 A1 | 2/2007 | Seidel et al. | |
| 2008/0039680 A1 | 2/2008 | Graham | |
| 2008/0118908 A1 | 5/2008 | Dozortsev | |
| 2009/0101507 A1 | 4/2009 | Aitken et al. | |
| 2010/0122359 A1 | 5/2010 | Suh et al. | |
| 2012/0028079 A1 | 2/2012 | Alfonta et al. | |

FOREIGN PATENT DOCUMENTS

| | | |
|---|---|---|
| AU | 2004/278448 A1 | 4/2005 |
| AU | 2004/278448 B2 | 4/2005 |
| WO | WO 2005/033295 A1 | 4/2005 |

OTHER PUBLICATIONS

C. Ainsworth, et al. "Development of novel electrophoretic system for the isolation of human spermatozoa" Human Reproduction, vol. 20, No. 8, Aug. 2005, p. 2261-2270.*

Ainsworth, et al.; The electrophoretic separation of spermatozoa: an analysis of genotype, surface carbohydrate composition and potential for capacitation; ; Int J Androl 34(5pt.2); May 12, 2011; e422-e434; European Academy of Andrology.

(Continued)

*Primary Examiner* — J. Christopher Ball
(74) *Attorney, Agent, or Firm* — Thorpe North & Western, LLP

(57) ABSTRACT

The present invention provides methods, devices, and kits for separating and selecting top sperm from a sperm sample of a subject. In one aspect, for example, such a method can include removing a portion of negatively charged protein from sperm in the sperm sample, immobilizing the sperm, electrophoretically separating the sperm, and selecting mature sperm based on electromotility properties.

16 Claims, 3 Drawing Sheets

(56) References Cited

OTHER PUBLICATIONS

Ainsworth, et al.; Development of a novel electrophoretic system for the isolation of human spermatozoa; *Hum Reprod* 20 (8); Apr. 14, 2005; 2261-2270: European Society of Human Reproduction and Embryology/Oxford Journals.

Ainsworth, et al.; First recorded pregnancy and normal birth after ICSI using electrophoretically isolated spermatozoa; *Hum Reprod* 22 (1); Sep. 13, 2006; 197-200; European Society of Human Reproduction and Embryology/Oxford Journals.

Aitken, et al.; Electrophoretic sperm isolation: optimization of electrophoresis conditions and impact on oxidative stress; *Hum Reprod* 26(8); Jun. 10, 2011; 1955-1964: European Society of Human Reproduction and Embryology/Oxford Journals.

Calzada, et al.; Presence and chemical composition of glycoproteic layer on human spermatozoa (Abstract); *Arch Androl* 33 (2); Jan. 1994; 87-92 (Abstract 2 pages); Taylor & Francis.

Chan, et al.; A simple zeta method for sperm selection based on membrane charge; *Fertil Steril* 85(2); Feb. 2006; 481-486; American Society for Reproductive Medicine.

Giuliani, et al.; Expression of gp20, a human sperm antigen of epididymal origin is reduced in spermatozoa from subfertile men; *Mol Reprod Dev* 69 (2); Oct. 2004; 235-240; Wiley Periodicals Inc.

Holt; Membrane heterogeneity in the mammalian spermatozoon (Abstract); *In Rev Cytol* 87; 1984; 159-194 (Abstract 2 pages); Elsevier Inc.

Ishijima, et al.; Zeta potential of human X- and Y- bearing sperm (Abstract); *Int J Androl* 14 (5); Oct. 1991; 340-347 (Abstract 1 page); European Academy of Andrology.

Kallajoki et al.; Surface lycoproteins of human spermatozoa; *J Cell Sci* 82; 067/01/1986; 11-22; The company of Biologists.

Kam et al.; Retention of membrane charge attributes by cryopreserved-thawed sperm and zeta selection; *J Assist Reprod Genet* 24 (9); Sep. 2007; 429-434; Springer US.

Kirchhoff and Schroter; New insights into the origin, structure and role of CD52: A major component of the mammalian sperm glycocalyxn (Abstract); *Cells Tissues Organs* 168 (1-2); 2001; 93-104 (Abstract 2 pages); Karger Medical and Scientific Publications.

Naz, et al; Monoclonal antibody to a human germ cell membrane glycoprotein that inhibits fertilization (Abstract); *Science* 22 (4659); 1984; 342-344 (Abstract 1 page); American Association for the Advancement of Science/Highwire Press.

Schroter, et al.; Male-specific modification of human CD52; *J Biol Chem* 274 (42); Oct. 15, 1999; 29862-29873; American Society of Biochemistry and Molecular Biology.

PCT Application PCT/US2013/056490; filed Aug. 23, 2013; Douglas T. Carrell, et al.; International Search Report mailed Dec. 23, 2013.

\* cited by examiner

SPERM SEPARATION DEVICES AND ASSOCIATED METHODS

PRIORITY DATA

This application claims the benefit of U.S. Provisional Patent Application Ser. No. 61/692,647, filed on Aug. 23, 2013, which is incorporated herein by reference.

FIELD OF THE INVENTION

The present invention relates to devices and mechanisms for separating and selecting sperm for fertility or other reasons. Accordingly, the present invention involves the fields of reproductive biology, medicine, and molecular biology.

BACKGROUND OF THE INVENTION

Infertility is a specific area of reproductive medicine that continues to generate much interest. It is estimated in the United States alone that 6.7 million women between 15 and 44 have impaired fecundity. Additionally, it is estimated that 1 in every 136 men in the United States experiences infertility issues. Fertility treatments, including in vitro fertilization have been developed. In some cases, it is hopeful that genetically fit/top sperm can be isolated from the ejaculate to increase the chances of in vitro fertilization. It has proven difficult, however, for such sperm to be isolated due to the complex biochemical and physiological makeup of such cells. The separation process is further complicated by the difficulties inherent in identifying and separating sperm based on maturity and morphology. These two factors have been shown to improve in vitro fertilization success, particularly given the sheer number of cells in a typical sample.

SUMMARY OF THE INVENTION

Accordingly, aspects of the invention provide methods, devices, and kits for separating and selecting top sperm from a sperm sample of a subject. In one embodiment, such as method may include removing a portion of negatively charged protein from sperm in the sperm sample, immobilizing the sperm, electrophoretically separating the sperm, and selecting mature sperm based on electromotility properties.

In another aspect, an exemplary device for separating and selecting top sperm from a sperm sample of a subject may include a housing having a liquid reservoir operable to receive a sperm sample and an anode and a cathode positioned to generate an electric field or current through the liquid reservoir during use.

In a further aspect, and exemplary kit for separating and selecting top sperm from a sperm sample of a subject may include a device as recited herein and instructions describing how to separate and select top sperm from a sperm sample, and optionally a power source for generating an electric field between the anode and the cathode during use.

DETAILED DESCRIPTION

Figure 1:
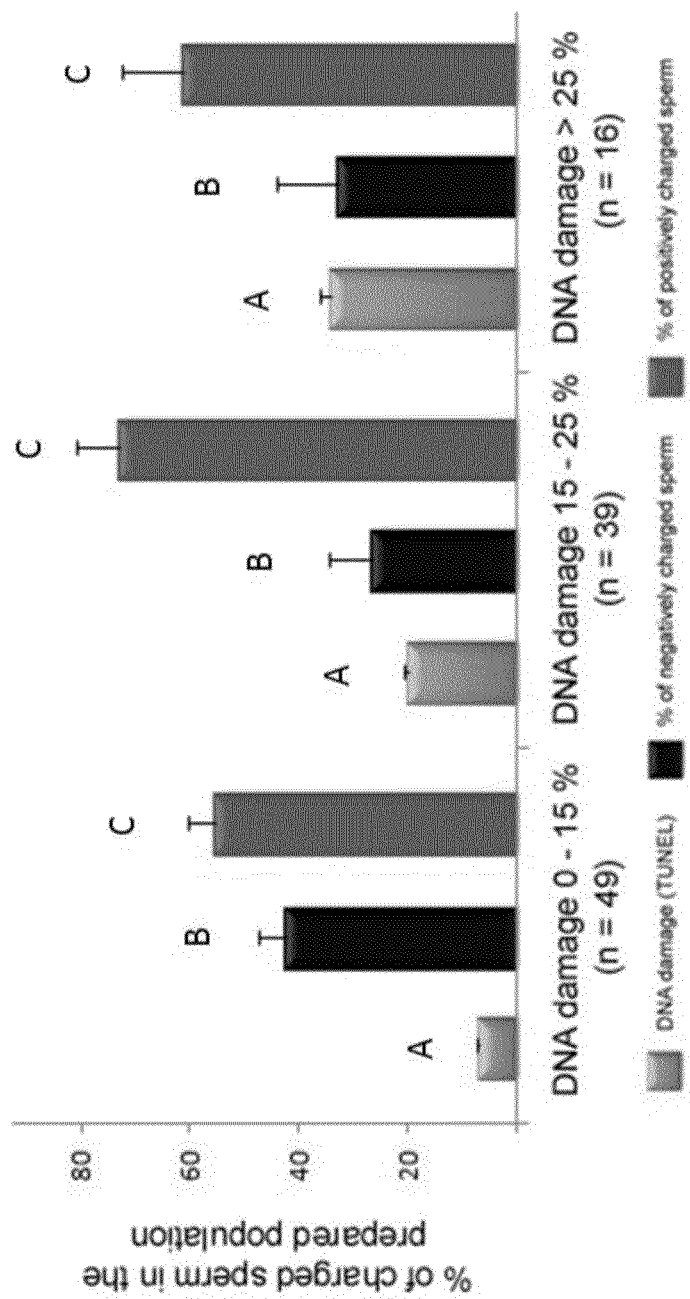
FIG. 1 is a graphical representation showing charge associated with DNA damage (A), negatively charged sperm (B), and positively charged sperm (C) in a prepared population.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a surface" includes one or more of such surfaces, and reference to "the electrode" includes reference to one or more of such electrodes.

DEFINITIONS

In describing and claiming the present invention, the following terminology will be used in accordance with the definitions set forth below.

As used herein, "subject" refers to a male mammal. Examples of subjects include humans, and may also include other animals such as horses, pigs, cattle, dogs, cats, rabbits, and aquatic mammals.

As used herein, "top sperm" refers to sperm that are mature, morphologically normal, viable, genetically normal and have a high fertilization potential.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and includes only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in an electrical or nonelectrical manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

Reference throughout this specification to "an example" of "an aspect" means that a particular feature, structure, or characteristic described in connection with the example or aspect is included in at least one embodiment. Thus, appearances of the phrases "in an example" or "in an aspect" in various places throughout this specification are not necessarily all referring to the same embodiment.

As used herein, the terms "substantial" and "substantially" refer to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Invention

The inventors have discovered various devices and methods for separating and identifying top sperm (preferable sperm) from a sperm sample. By utilizing the current devices and methods, sperm can be rapidly separated according to maturity, morphology and viability. Additionally, in some aspects sperm separation and oocyte fertilization can be accomplished at a same location, such as, for example, the same dish or container under a microscope.

As sperm is moving through the epididymis during spermatogenesis, negatively charged proteins (e.g. CD52, highly sialated glycosylphosphatidylinositol anchored protein) are attached to the surface of the sperm. These negatively charged proteins function to repel sperm from one another to prevent clumping. More mature sperm have spent more time moving through the epididymis and thus have a higher content of negatively charged protein attached thereto. Mature sperm often have a surface potential of, for example, about −16 to −20 mV.

Additionally, the percentage of sperm with DNA damage is generally inversely proportional to the percent of negatively charged sperm, and directly proportional to the percent of positively charged sperm in a sample, as can be seen in FIG. 1. DNA damage can be measured by a variety of techniques, including detecting DNA fragmentation by labeling the terminal end of nucleic acids by terminal deoxynucleotidyl transferase dUTP nick end labeling (TUNEL). TUNEL is a method for detecting DNA fragmentation that results from apoptotic signaling cascades. The assay relies on the presence of nicks in the DNA that can be identified by terminal deoxynucleotidyl transferase or TdT, an enzyme that will catalyze the addition of dUTPs that are secondarily labeled with a marker. It may also label cells that have suffered severe DNA damage.

Accordingly, selecting sperm based on negative charge can result in a higher proportion of mature sperm having the lowest amount DNA damage in the population. However, a majority of sperm acquire at least some negatively charged protein when moving through the epididymis, and thus a majority of sperm in the ejaculate are negatively charged to at least a certain degree, making it challenging to identify the most negative sperm in the population.

Figure 2:
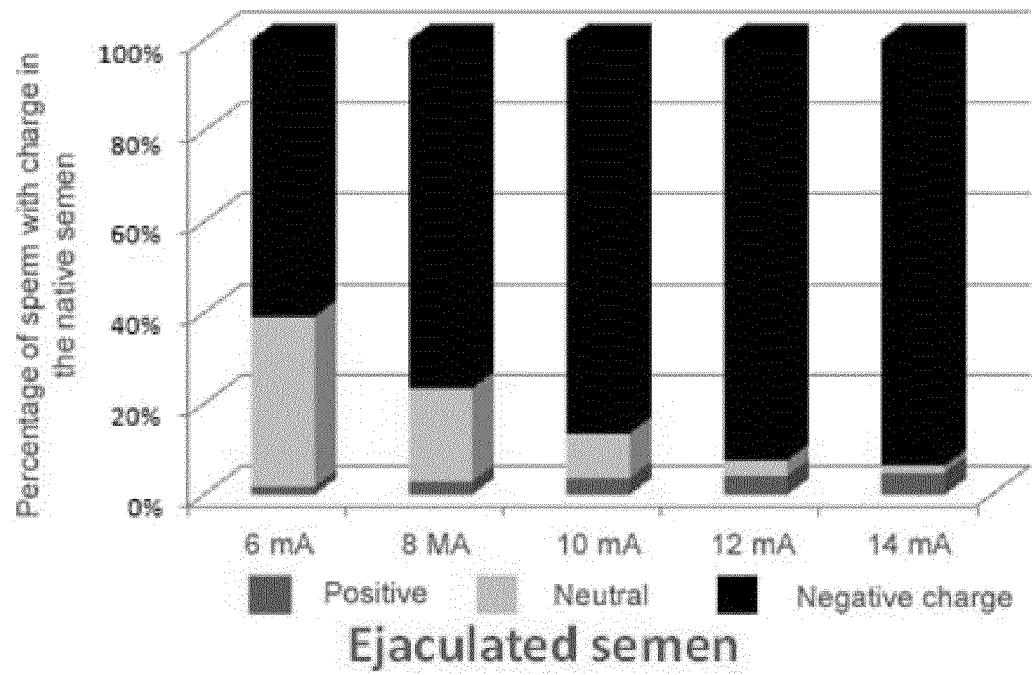
FIG. 2 is a graphical representation showing movement of neat sperm (i.e. untreated ejaculate) when subjected negative fields or currents of increasing strength.

As is shown in FIG. 2, for example, sperm are shown neat (i.e. unaltered ejaculated semen) and quantified as negative, neutral, or positive based on the direction of movement of the sperm in an electric field or current. As can be seen in the graph, the proportion of the population moving in the negative direction increases as the current of the electric field increases. Thus as current increases there is little or no selectivity between sperm of differing charge and it is difficult to select the most mature (i.e. most negatively charged) sperm. The inventors have discovered, however, that sperm separation based on negative charge can be paradoxically improved by removing a proportion of the negatively charged protein from the population of sperm cells.

Figure 3:
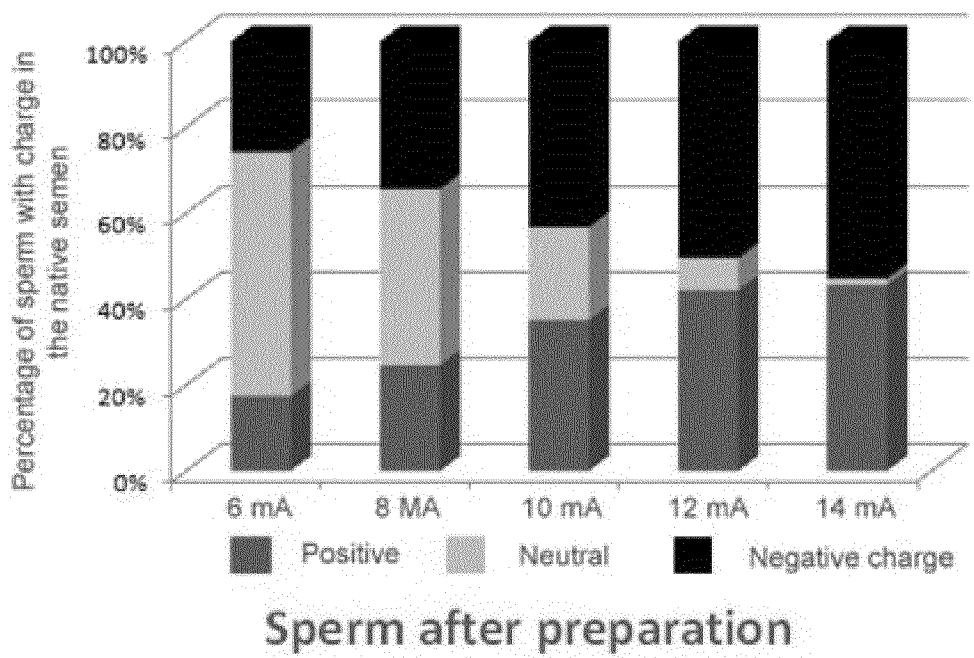
FIG. 3 is a graphical representation showing movement of sperm treated in accordance with one aspect of the present invention when subjected to negative fields or currents of increasing strength.

As can be seen in FIG. 3, sperm prepared in accordance with aspects of the present invention have a much broader distribution in the electric field or current, thus improving the selection of sperm based on maturity, which can include amount of negative charge. Additionally, it is of note that treating sperm in accordance with embodiments of the present invention tend to remove salicylic acid residues, that not all sperm loses their (−ve) charge, that there is an increase in the amount of sperm with a positive charge, and that about 10% of the population don't have negatively charged sperm when subjected to density gradient centrifugation (DGC). In some aspects, the sperm preparation process may remove other undesirable negatively charged moieties on the outside of the sperm that are not native to or otherwise impair the function or desirability of mature sperm. While several specific mechanisms for removing negatively charged entities from sperm are set forth herein, it is to be understood that nearly any mechanism capable of removing negatively charged entities without otherwise harming sperm can be used.

As such, in one aspect a method of separating and selecting top sperm from a sperm sample of a subject can include removing a portion or proportion of negatively charged protein across all or substantially all sperm in the sample. Thus, immature sperm initially having a low proportion of bound negatively charged protein can have some or all negatively charged protein removed, thus lowering the overall negativity of such sperm cells, and in some cases rendering them neutral or positively charged. It is contemplated that some sperm in the sample may have little or in some cases no negatively charged protein, and thus will be unaffected or rendered positive by the protein removal process. More mature sperm have a higher proportion of negatively charged protein and thus remain more negative following the protein removal process. Depending on the maturity of each cell, the remaining negative charge may be distributed throughout a range of negativities. The more mature sperm will have retained more negative charge from the negatively charged protein removal process as compared to less mature sperm, and therefore will move more rapidly toward the positive electrode. Positively charged immature sperm, on the other hand, will move toward the negative electrode, while sperm of an intermediate maturity will move toward either electrode at a slower speed based on the amount of negatively charged protein remaining.

Negatively charged protein can be removed from the sperm by any known technique, and any such technique that results in top sperm separation or segregation from other sperm is considered to be within the present scope. In one aspect, negatively charged protein can be partially or proportionally removed by centrifugation, such as, for example, density gradient centrifugation (DGC). As has been described, it is useful to maintain at least a portion of the negatively charged protein on the sperm cells to allow adequate separation in the electrical gradient, and as such, conditions for removal of negatively charged protein can vary depending on a variety of factors, including design choice.

In one specific aspect, the proportion of negatively charged protein can be removed from the sperm by forcing the cells through two gradients: a top gradient having a low density and a bottom gradient having a high density. Dead sperm and debris do not move into the high density region. Other medium can be utilized as well. Centrifuging the sperm in water will remove a portion of the negatively charged protein but will not cause separation to occur. Additionally, other methods such as vortexing and sonication can be used to remove protein in an appropriate medium. Further separation can then occur in an electric field or current. Despite these specific examples, nearly any other mechanism for removing negatively charged proteins or other substances from the sperm can be used.

As has been described, the amount of negatively charged protein associated with a sperm cell is an indicator of maturity of the sperm. As such, sperm can be separated based on charge characteristics that can relate to maturity. So, applying an electrical field or current to the sperm sample will cause a separation of sperm based on charge, and thus mature sperm are separated from less mature sperm.

In another aspect, a method of separating and selecting top sperm from a sperm sample of a subject can include removing a portion of negatively charged protein from sperm in the sperm sample, immobilizing the sperm, and electrophoretically separating the sperm. Once separated, top sperm can be selected based on their electromotile properties.

One caveat that can arise during separation relates to the swimming motion of sperm cells. Progressively motile sperm swimming against the electrical field or current can be incorrectly measured by the separation process as having a lower negative charge as compared to progressively motile sperm swimming with the electrical field. While not necessary, in some embodiments of the invention inactivating the movement mechanisms of sperm can thus increase the effectiveness of the electrical separation process by eliminating sperm-derived movement artifacts. Alternatively, current adjustments and compensation can be used in some cases when the sperm is not immobilized.

The immobilization of sperm can be accomplished by a variety of techniques, and any technique capable of such immobilization that is compatible with the present purposes is considered to be within the present scope. For example, in one aspect the sperm can be suspended in a deionized liquid, such as deionized water to cause immobilization. The lack of ions required for sperm to swim in the deionized liquid thus causes immobility. In another aspect, mitochondria in the sperm can be inactivated using a mitochondrial poison to cause immobility. Furthermore, sonication can be used to immobilize the sperm among other mechanisms. Nearly any other medium suitable for immobilizing sperm, or mechanism for immobilizing sperm can be used in the present invention.

In addition to selection by negativity, morphological selection can also be used to select top sperm cells from the sample. As such, sperm cells showing high negativity can be observed and selected based on having an appropriate morphology. Non-limiting examples of desirable morphology can include symmetry, head diameter, the lack of pits or dents in the head, and the like. These cells, once selected by negativity, morphology, or both, can be utilized to fertilize an oocyte. In addition, negativity, morphology, and motility can be used either separately or collectively for selection of sperm. In some aspects, the oocytes can be present in the separation apparatus, and thus the fertilization can be performed quickly and efficiently at the point of sperm separation and selection. In other words, separation and fertilization can occur in the same apparatus.

The sperm can be manipulated following selection by a variety of devices and techniques. In one aspect, for example, sperm can be selected and isolated using a suction pipette, capillary tube, or other needle device. In another aspect, the sperm can be picked up using an intracytoplasmic sperm injection (ICSI) needle. One advantage of using such a device can include the immediate fertilization of an oocyte using the ICSI needle containing the selected sperm.

A variety of designs are contemplated for a sperm separation device according to aspects of the present disclosure. Generally, however, the device can include a housing having a reservoir for containing a liquid medium into which the sperm are introduced, and a pair of electrodes positioned for generating an electric field or current through the reservoir. In some aspects, the reservoir can be a disposable portion separate from the electrodes. Such a disposable reservoir can be positioned between the electrodes during a separation procedure, and then removed for disposal once the procedure is completed, allowing reuse of the electrodes. In other aspects, the electrodes can be disposable along with the housing.

A variety of housing materials are contemplated, and any material useful for the construction and use of such a device is considered to be within the present scope. In one aspect, the housing material can be transparent, thus allowing microscopic viewing of the separation. A variety of transparent materials are contemplated, and any such material is considered to be within the present scope. Such materials can include various polymers, glass, quartz, and the like. In some aspects, the material can either be, or be coated with a material having a very low frictional coefficient. A low degree of friction between the sperm and the material allows for better movement of sperm when subjected to the electric field or current. One example of a low friction material is polytetrafluroethylene. In some embodiments a material with a frictional coefficient below about $0.8\mu_s$ may be used. In another aspect, the frictional coefficient may be less than about $0.1\mu_s$. In yet another aspect, the coefficient may be below about $0.05\mu_s$.

In some aspects, reduced friction between sperm and the device can be achieved with the addition of reagents or other liquid materials. In one example, water can be used. In another example, bovine serum albumin (BSA) can be used. In yet further examples, synthetically produced buffers can be used. Notably, in some aspects the sperm can be exposed to, coated with, or otherwise "primed" with such materials before or during the electrophoresis separation process and carry such materials with them into the device.

The amount of current or intensity of electric field or current used can also be varied in order to achieve specific results and obtain selection of desired sperm. In some aspects as noted below, the specific electric field or current intensity selected may be in proportion to the space between the electrodes and kept within certain ratios. However, generally speaking, the intensity may be from about 0 to about 300 mA, or about 0 to about 300 volts, or about 0 to about 75 watts. In another aspect, the intensity may be from about 1 to about 400 mA, 1 to about 300 volts or about 1 to about 75 watts. In addition, in some aspects, the amount may be between about 4 and 20 mA. In further aspects, the amount may be 6, 8, 10, 12, or 14 mA.

Figure 4:
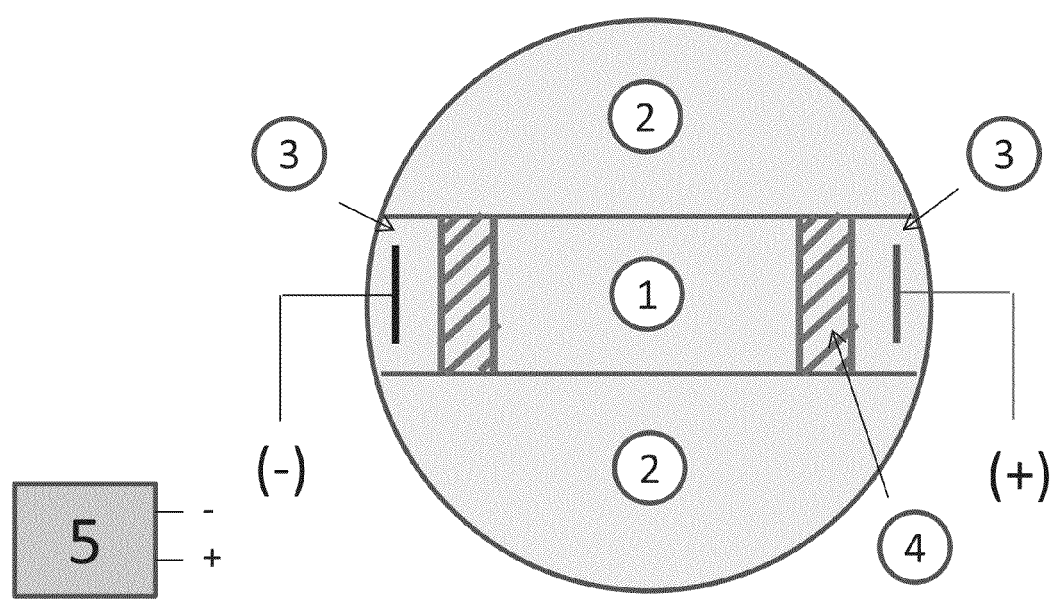
FIG. 4 is a schematic view of an embodiment of a sperm separation device.

In one specific aspect, a potential design for a sperm separation device is shown in FIG. 4. Such a device can include a housing having a liquid reservoir 1 operable to receive a sperm sample, and electrodes 3 positioned to generate an electric field through the liquid reservoir 1 during use. As such, a sperm sample can be introduced into the liquid reservoir 1 and separated within the electrical field generated between the two electrodes. FIG. 4 also shows a separation matrix 4 to facilitate a uniform electric field and to prevent sperm from reaching the electrodes. Such membranes and/or other structures can also reduce liquid movement within the reservoir that may skew the charge separation procedure. In some cases the electrodes can heat the adjacent liquid, and cause thermal movement or movement due to bubble creation. The separation matrix can reduce or eliminate such movement. The separation matrix can be made from any material that is conductive and can preclude liquid movement and/or sperm from reaching the electrodes. Non-limiting examples of such materials can include porous polymers, agarose, perforated metals or metal foil, and the like. In some aspects the separation matrix can be solid and impermeable, and in some cases nonconductive. Such a matrix can include a conductive bridge such as a salt bridge or a metal conductor electrically coupling the liquid surrounding the electrodes with the liquid of the reservoir.

A power supply 5 can be electrically coupled to the electrodes 3 to generate the electric field. The power supply can be physically coupled to the housing, or the power supply can be distinct from the housing. Additionally, in some aspects the housing can have a lid to cover the liquid reservoir and thus improve the sterility of the liquid environment.

Additionally, a device such as shown in FIG. 4 can be used to separate and select top sperm, and to function as a fertilization platform at the same time. Incorporating these processes can reduce the chances for contamination and gamete damage, as well as providing a more cost effective solution to various fertilization issues. As one example, the regions show at 2 in FIG. 4 can be used to hold and fertilize oocytes following sperm separation and selection.

As has been described, a device containing separation electrodes can include structures or internal design features to minimize movement of the surrounding fluid that may negatively affect the separation process. For example, baffle or wall structures can be included in the device to minimize fluid movement. In another aspect, the separation apparatus can include multiple chambers to minimize fluid movement.

In additional embodiments, the device can be of nearly any shape or size suitable to accomplish a specifically desired result. For example, the device can be square, rectangular, triangular, oval, etc. and can have any needed or desired size. Furthermore, distance between electrodes either in relationship or not in relationship to the size of the device can be employed. In certain aspects, the intensity of the electric field or current may be varied with the distance between the electrodes. In some aspects, the distance and intensity may be attuned to a ratio that maximizes movement of the most negatively charged sperm. In other cases the ration may be attuned to minimize movement of the least negatively charged sperm. In yet other cases, the ratio is selected to maximize movement of the most negatively charged sperm while minimizing movement of the least negatively charged sperm. Again, size and shape of the present device may customized in support of obtaining desired ratios.

In another aspect, the present disclosure can include a kit for separating and selecting top sperm from a sperm sample of a subject. Such a kit can include a housing having a liquid reservoir operable to receive a sperm sample, and an anode and a cathode positioned to generate an electric field through the liquid reservoir during use. The kit can include instructions for use on how to separate and select top sperm from a sperm sample, and in some cases a visualization chart of various sperm morphologies with appropriate descriptions. The kit can also include sterile packaging so as to keep the device sterile and untainted prior to opening of the package and use. Optionally, a kit may include any reagents, chemicals, buffers, or liquids (such as deionized water or BSA) that are desirable for use in washing and immobilization the sperm and for sperm separation. Such items can be provided in either a liquid or solid form. In some aspects, the kit can also include a power source for generating an electric field between the anode and the cathode during use. In some aspects, the device can have a power source integrated therein.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. A method of separating and selecting top sperm from a sperm sample of a subject, comprising:
   removing a portion of negatively charged protein from sperm in the sperm sample;
   immobilizing the sperm;
   electrophoretically separating the sperm; and
   selecting mature sperm based on electromotility properties.

2. The method of claim 1, further comprising selecting sperm based on morphological features.

3. The method of claim 2, further comprising selecting sperm on a combination of electromotility properties and morphological features.

4. The method of claim 1, wherein the sperm are immobilized with deionized.

5. The method of claim 1, wherein the process of removing a portion of negatively charged protein from sperm comprises washing the sperm with water.

6. The method of claim 1, wherein the process of removing a portion of negatively charged protein from sperm includes density gradient centrifugation of the sperm.

7. The method of claim 1, further comprising priming the sperm with a primer to reduce friction on the sperm during separation.

8. The method of claim 1, wherein the electromotility properties are indicative of an amount of negative charge remaining on each sperm.

9. The method of claim 7, wherein sperm which are most highly negatively charged in the sample are selected.

10. The method of claim 1, wherein sperm in the sample that are highly negatively charged have only a portion of the negative charge removed and sperm in the sample that are moderately or slightly negatively charged have substantially all of the negative charge removed.

11. A device for separating and selecting top sperm from a sperm sample of a subject, comprising:
    a housing having a liquid reservoir operable to receive a sperm sample; and
    an anode and a cathode positioned to generate an electric field through the liquid reservoir during use, wherein the amount of electricity applied to the electrodes is from about 4 mA to about 20 mA.

12. The device of claim 11, further comprising at least one separation matrix positioned to preclude sperm from reaching the anode or the cathode.

13. The device of claim 11, wherein the electrodes are positioned substantially opposite from one another so as to draw sperm with a negative charge in a direction away from sperm with a positive charge.

14. The device of claim 11, further comprising a bubble restriction chamber near one or more electrodes to prevent bubble formed from affecting sperm movement.

15. The device of claim 11, further comprising at least one oocyte injection chamber.

16. The device of claim 11, wherein the device is disposable.

* * * * *